United States Patent [19]

Wilk

[11] Patent Number: 5,415,167
[45] Date of Patent: May 16, 1995

[54] MEDICAL SYSTEM AND ASSOCIATED METHOD FOR AUTOMATIC DIAGNOSIS AND TREATMENT

[76] Inventor: Peter J. Wilk, 185 W. End Ave., New York, N.Y. 10023

[21] Appl. No.: 941,569

[22] Filed: Sep. 8, 1992

Related U.S. Application Data

[63] Continuation-in-part of Ser. No. 819,120, Jan. 10, 1992.

[51] Int. Cl.[6] .............................. A61B 5/00; A61B 8/08
[52] U.S. Cl. ............................. 128/653.1; 128/659; 128/660.03; 128/660.07; 128/630; 128/903; 128/904; 340/573
[58] Field of Search ............... 128/653.1, 653.2, 659, 128/660.07, 903, 904, 660.03, 630; 606/191, 192, 194; 340/573; 364/413.22; 382/6

[56] References Cited

U.S. PATENT DOCUMENTS

| | | | |
|---|---|---|---|
| 4,567,898 | 2/1986 | Plugge et al. | 128/660.07 |
| 4,945,478 | 7/1990 | Merickel et al. | 128/413.22 |
| 4,981,139 | 1/1991 | Pfohl | 128/671 |
| 5,003,984 | 4/1991 | Muraki et al. | 128/904 |
| 5,022,402 | 6/1991 | Schieberl et al. | 128/671 |
| 5,203,336 | 4/1993 | Iida et al. | 128/660.07 |
| 5,257,627 | 11/1993 | Rapoport | 128/904 |
| 5,289,824 | 3/1994 | Mills et al. | 128/904 |

FOREIGN PATENT DOCUMENTS

8601118  2/1986  European Pat. Off. ............ 128/904

Primary Examiner—Krista M. Pfaffle
Attorney, Agent, or Firm—R. Neil Sudol; Henry D. Coleman

[57] ABSTRACT

A medical method comprises the steps of scanning a predetermined internal organ of a patient to collect individualized dimensional data about the organ, digitizing the data, and automatically storing encoded structural dimensions of the organ at different times. Dimensions of the organ are automatically compared with previously stored dimensions to determine changes in the dimensions. A cognizable signal is automatically generated, at a remote facility or at the person of the patient, upon a determination that dimensions of the organ have changed so as to indicate a dangerous condition of the patient, such as a ruptured splenic hematoma or a ruptured aneurysm.

28 Claims, 6 Drawing Sheets

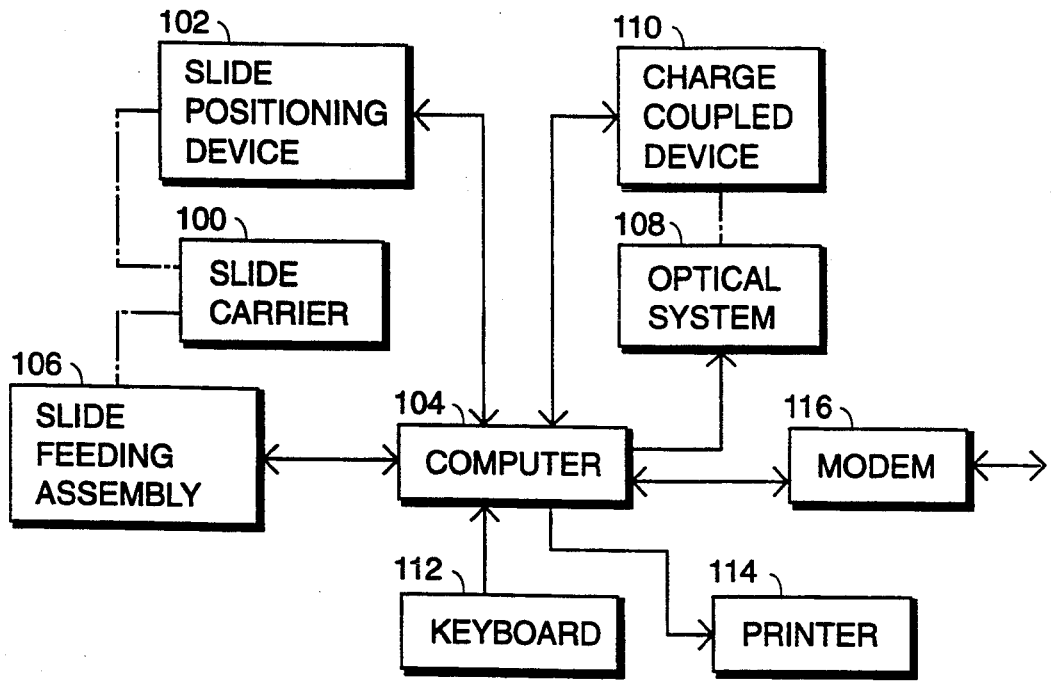
FIG. 5
FIG. 6
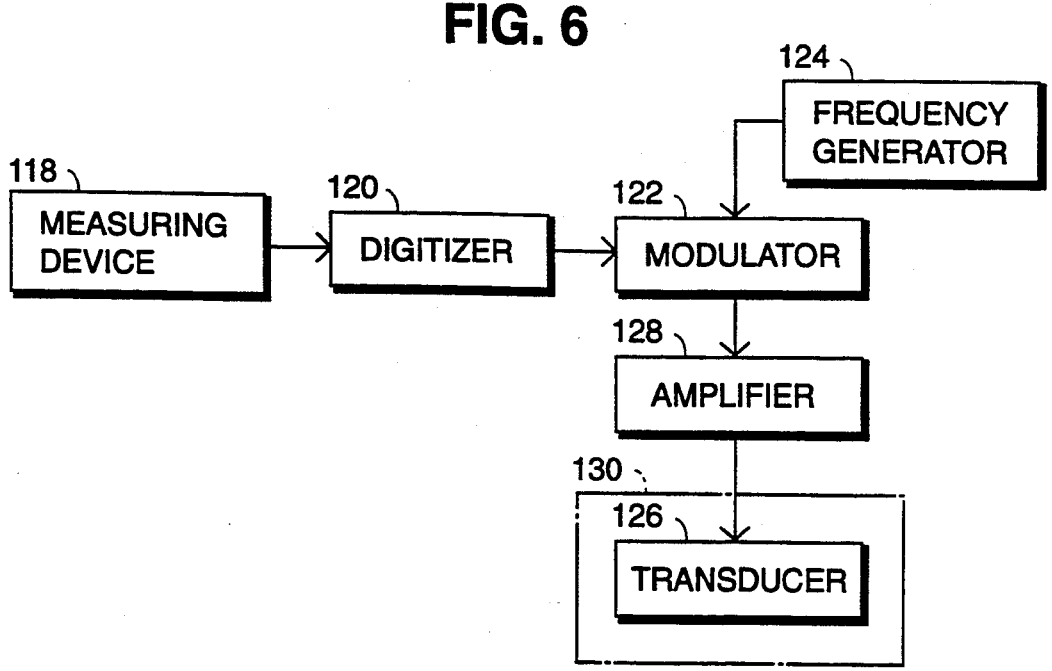
FIG. 7

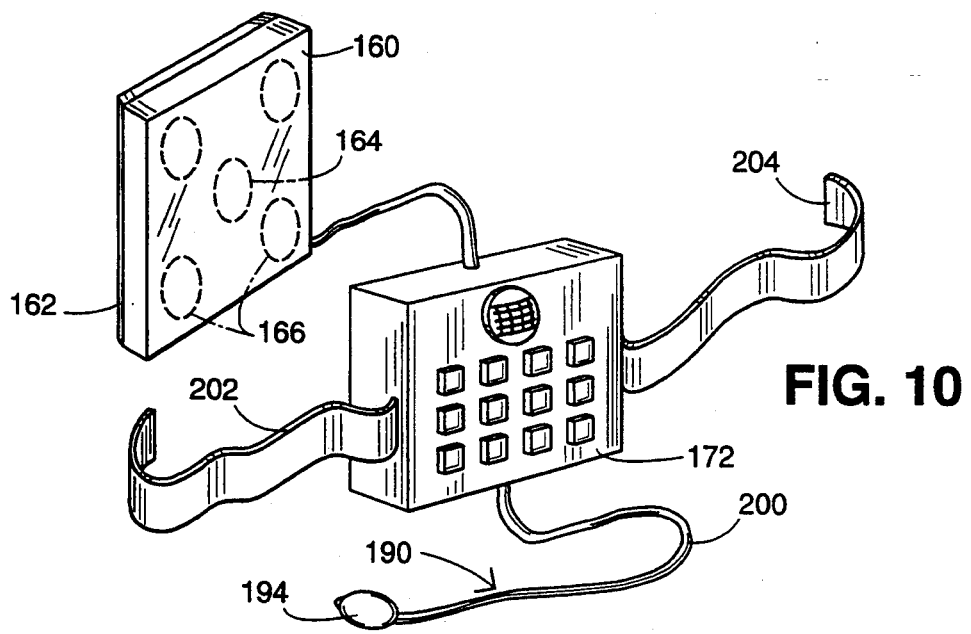
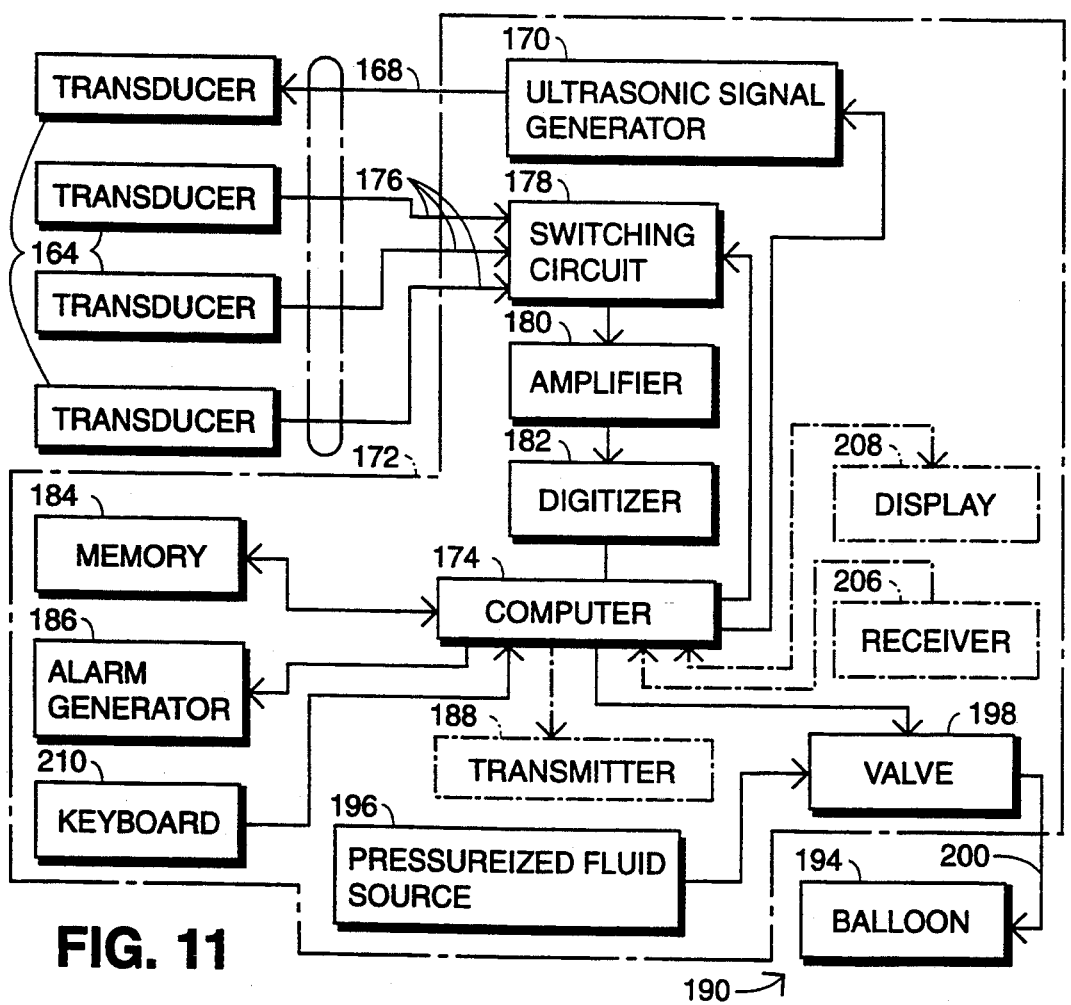

MEDICAL SYSTEM AND ASSOCIATED METHOD FOR AUTOMATIC DIAGNOSIS AND TREATMENT

CROSS-REFERENCE TO A RELATED APPLICATION

This application is a continuation-in-part of commonly owned application Ser. No. 819,120, filed Jan. 10, 1992.

FIELD OF THE INVENTION

This invention relates to a medical method for at least partially automatic diagnosis and, optionally, treatment. This invention also relates to a system for implementing such a method. More specifically, this invention relates to a method and an associated system for automatically diagnosing condition based on the sizes and dimensions of an internal organ of a patient and, optionally, for treating the condition to alleviate possible results thereof.

BACKGROUND OF THE INVENTION

When the spleen suffers a blunt trauma, a subcapsular hematoma frequently results. The hematoma may resolve itself naturally in the course of time. However, in some cases, the spleen ruptures and hemorrhaging occurs. The hemorrhaging may be fatal to the patient.

Because of the possible fatality, patients who have been diagnosed as having a spleen with a subcapsular hematoma are generally kept in a hospital and subjected regularly to scanning by a CAT scan or NMR apparatus. In each scan, the monitoring personnel compare the physical condition or dimensions of the spleen, and particularly the hematoma, with previously recorded or detected dimensions. In the event that the hematoma begins to increase in size, the patient is scheduled for immediate surgery.

Even with conscientious monitoring by hospital personnel, the spleens of such patients nevertheless rupture with disastrous consequences. Moreover, patients who are otherwise fine and whose splenic hemtoma eventually subsides roam the halls of hospitals and monopolize valuable bed space.

OBJECTS OF THE INVENTION

An object of the present invention is to provide a medical diagnostic system and a related diagnostic method.

A more particular object of the present invention is to provide such a diagnostic system and method which reduces medical diagnosis costs.

Another particular object of the present invention is to provide such a diagnostic system and method which can be used by persons having less training than traditional physicians.

A further particular object of the present invention is to provide an at least partially automated diagnostic system and method.

Another object of the present invention is to provide a method for automatically diagnosing structural changes in an internal organ of a patient.

Another object of the present invention is to provide such a method for automatically alerting hospital personnel of a possible fatal condition in a patient.

Another, more specific, object of the present invention is to provide such a method for automatically monitoring a spleen or a blood vessel for changes in structure signaling a possibly imminent spleen or aneurysm rupture.

A further specific object of the present invention is to provide a method for automatically instituting a treatment upon detection of an internal structural change.

Yet another object of the present invention is to provide a system or device for use in a method in accordance with the present invention.

These and other objects of the present invention will be apparent from the drawings and detailed descriptions herein.

SUMMARY OF THE INVENTION

A medical method in accordance with the present invention comprises the steps of (a) scanning a predetermined internal organ of a patient to collect individualized dimensional data about the organ, (b) digitizing the data, (c) automatically storing encoded structural dimensions of the organ at different times, (d) automatically comparing dimensions of the organ with previously stored dimensions of the organ to determine changes in dimensions of the organ, and (e) automatically generating a cognizable signal upon a determination that dimensions of the organ have changed so as to indicate a dangerous condition of the patient.

According to another feature of the present invention, the method further comprises the step of therapeutically affecting function of the organ to alleviate the possibly dangerous condition. More specifically, particularly in the case where a traumatized portion of a spleen or an aneurysm in a blood vessel is increasing in size, a step may be automatically undertaken to reduce blood flow to the organ. That step may be implemented by inflating a balloon in an artery feeding the organ to thereby block blood flow in the artery. The balloon is implanted in the patient prior to the scanning of the subject organ.

According to a further feature of the present invention, generation of the cognizable signal may be implemented by transmitting an electromagnetic signal over telephone lines to a remote monitoring facility. Pursuant to a specific feature of the present invention, the electromagnetic signal is a wireless signal, the step of transmitting includes the step of wirelessly transmitting the wireless signal.

The scanning of the internal organ may be accomplished by attaching a scanning device to the patient and operating the scanning device to determine dimensions of the organ.

According to an additional feature of the present invention, the method further comprises the steps of (a) transmitting the digitized data to a remote monitoring facility, (b) receiving instructions from the facility, and (c) manually moving the scanning device from one location to another in response to the instructions, each such location being juxtaposed to the patient.

According to yet another feature of the present invention, the scanning of the internal organ is achieved by generating an ultrasonic pressure wave, monitoring the pressure wave upon reflection thereof by internal organs, and generating an electrical signal encoding the reflected ultrasonic pressure waves.

Alternatively, the scanning of the internal organ may be implemented by automatically monitoring byproducts of radioactive decay. In this case, a radioactive substance is injected or otherwise dispensed within the body so as to be absorbed, for example, into the spleen. As the substance decays, the radioactive byproducts reveal the dimensions (shape, configuration, size) of the organ and its parts.

A medical system comprises, in accordance with the present invention, a scanner juxtaposable to a patient for collecting individualized dimensional data about a predetermined internal organ of the patient, a digitizer operatively connected to the scanner for digitizing the data, and a memory for storing encoded structural dimensions of the organ at different times. A computer is operatively connected to the memory and the digitizer for comparing dimensions of the organ with previously stored dimensions of the organ to determine changes in dimensions of the organ. An alarm generator is operatively connected to the computer for generating a cognizable signal upon a determination by the computer that dimensions of the organ have changed so as to indicate a possibly dangerous condition of the patient.

In accordance with another feature of the present invention, the system further comprises a treatment device operatively connected to the computer and adapted for implantation into the patient for therapeutically affecting function of the organ to alleviate the possibly dangerous condition upon the determination by the computer that dimensions of the organ have changed so as to indicate such possibly dangerous condition.

The treatment device may operate to at least partially reduce blood flow to the subject organ upon the determination by the computer that dimensions of the organ have changed so as to indicate a possibly dangerous condition. Specifically, the treatment device may take the form of a balloon disposable in an artery feeding the organ and an inflation component operatively connected to the balloon for inflating the balloon to block blood flow in the artery.

In accordance with another feature of the present invention, the alarm generator may include a transmitter for transmitting to a remote monitoring facility an electomagnetic signal encoding the change in dimensions of the organ. The electromagnetic signal may be a wireless signal.

Preferably, the scanner is portable, the system further comprising a fastener for attaching the scanner to the patient. In such a portable system, the digitizer, the memory, and the computer are all mounted to a housing.

In accordance with an additional feature of the present invention, the scanner includes an electroacoustic transducer for generating an ultrasonic pressure wave and an acoustoelectric transducer for generating an electrical signal encoding reflected ultrasonic pressure waves received by the scanner.

Alternatively, the scanner includes a monitor for detecting byproducts of radioactive decay.

A method in accordance with the present invention serves in the automatic diagnosis of structural changes in an internal organ of a patient. Such changes change be detected immediately. Accordingly, the method is particularly effective where a change in size is sudden and may not be timely detected by conventional monitoring procedures. Hospital personnel are automatically and immediately alerted as to a possible fatal condition in a patient such as an imminent spleen or aneurysm rupture.

A method in accordance with the present invention automatically institutes a treatment such as the blockage of blood flow to or through the subject organ, thereby minimizing hemorrhaging prior to treatment by surgeons.

BRIEF DESCRIPTION OF THE DRAWING

FIG. 5 is a diagram showing the composition of a data string or module used in the system of FIG. 4.

FIG. 6 is a block diagram of a computerized slide scanning system.

FIG. 7 is a block diagram of a device for measuring a diagnostic parameter and transmitting the measurement over the telephone lines.

FIG. 10 is a schematic perspective view of a system for automatically diagnosing and treating internal structural changes signifying imminent dangerous conditions.

FIG. 11 is a block diagram of the system of FIG. 10.

DETAILED DESCRIPTION

Figure 1:
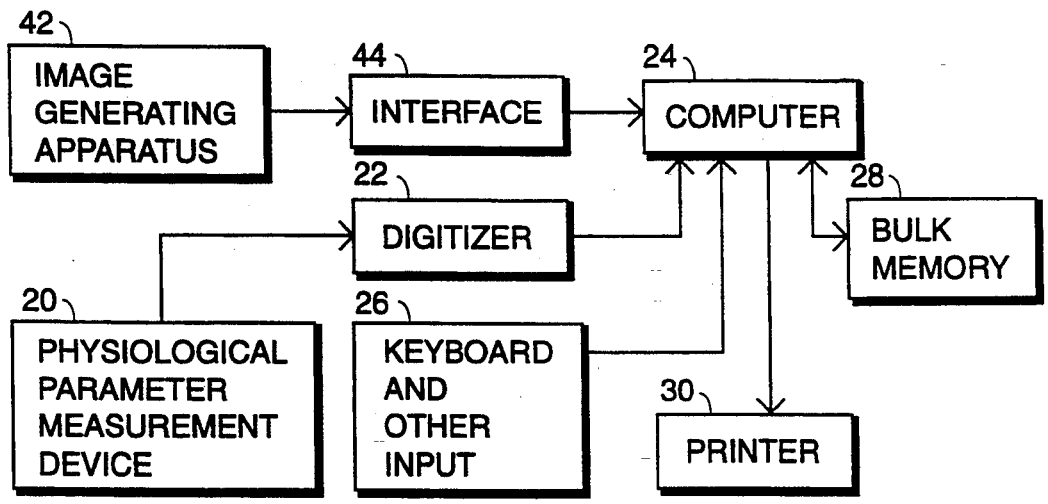
FIG. 1 is a block diagram of a medical diagnostic system.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a doppler study apparatus, an EEG machine, an EKG machine, an EMG machine, or a pressure measurement device, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
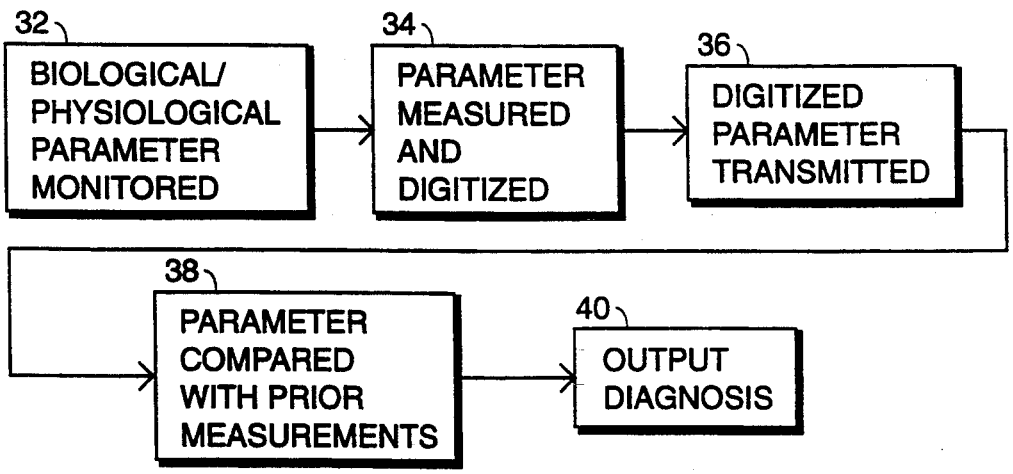
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, then computer 28 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, an image generating apparatus or scanner 42 for generating in electrically encoded form a visually readable image of an organic part of the patient. Scanner 42 may take the form of an MRI apparatus, a CAT scanner, an X-ray machine, an ultrasonography apparatus, or a video camera with or without magnification optics for magnifying a sample on a slide. The video camera can be used for obtaining an image of a portion of a patient's skin.

Scanner 42 is connected via an interface 44 to computer 24.

Figure 3:
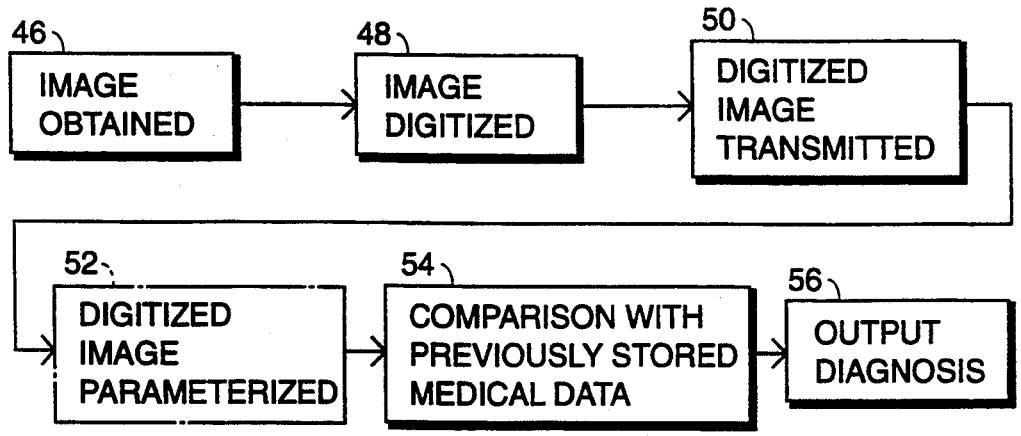
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 30 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus or CAT scanner, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 40 (FIG. 3), computer 24 communicates the results of its diagnostic evaluation to a user or patient.

Figure 4:
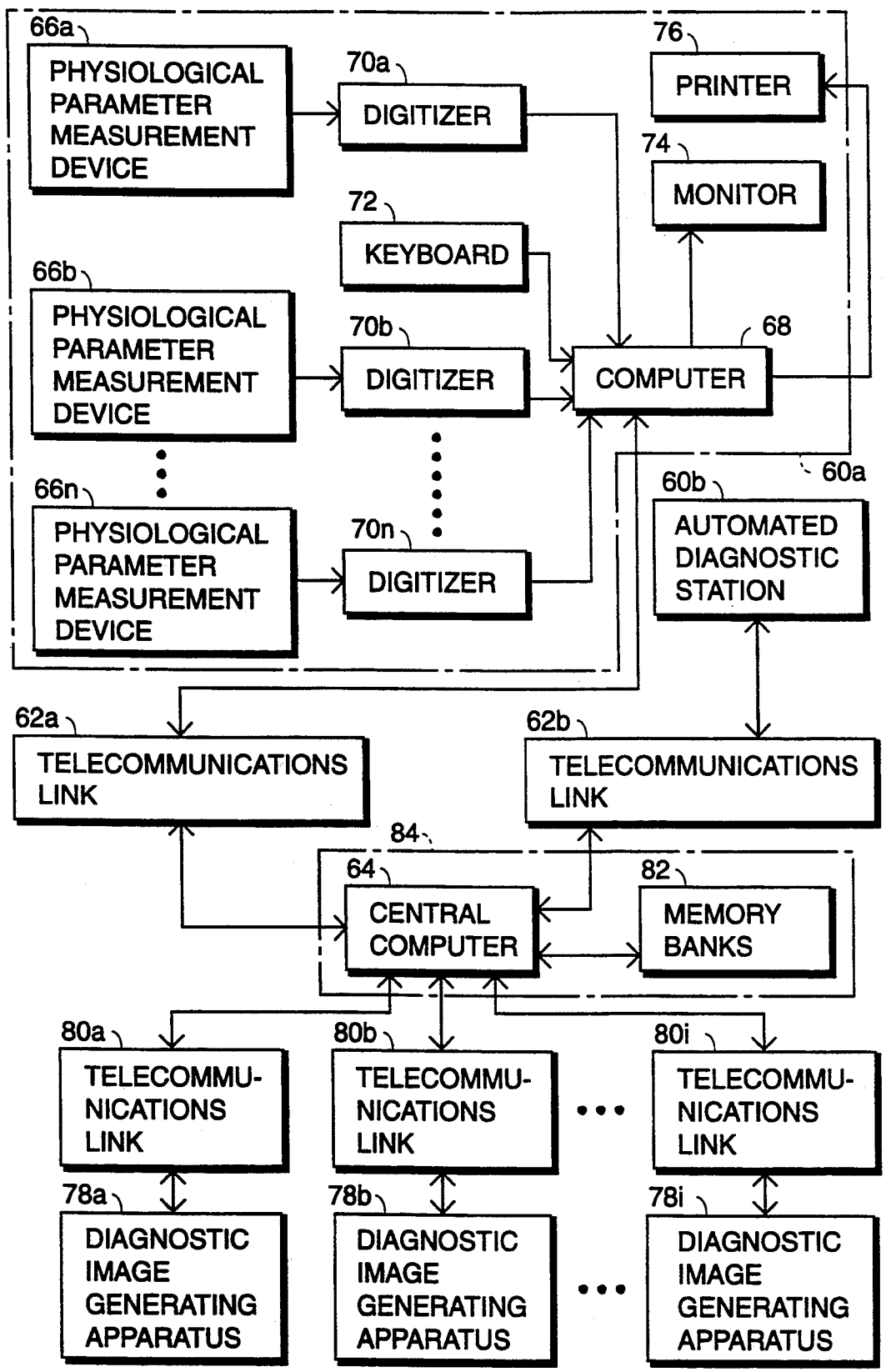
FIG. 4 a block diagram of a further medical diagnostic system.

As illustrated in FIG. 4, a medical diagnostic system comprises a plurality of remote automated diagnostic stations 60a and 60b connected via respective telecommunications links 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b, . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, . . . 66n is juxtaposable to a patient for collecting individualized medical data about the patient's condition. Monitoring and measuring devices 66a, 66b, . . . 66n may respectively take the form of an electronic thermometer, an electronic blood pressure gauge, a pulmonary function apparatus, a doppler study apparatus, an EEG machine, an EKG machine, an EMG machine, or a pressure measurement device, etc.

Digitizers 70a, 70b, ... 70n convert normally analog type signals into coded binary pulses and transmit the resulting digital measurement signals to computer 68. Digitizers 70a, 70b, ... 70n may be incorporated into the housings or casing (not shown) enclosing all or part of the respective monitoring and measuring devices 66a, 66b, ... 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, ... 78i are also connected to central computer 64 via respective telecommunications links 80a, 80b, ... 80i. Scanners 78a, 78b, ... 78i each generate in electrically encoded form a visually readable image of an organic part of the patient. Scanners 78a, 78b, ... 78i may each take the form of an MRI apparatus, a CAT scanner, an X-ray machine, an ultrasonography apparatus, or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

As illustrated in FIG. 5, local computers 24 and 68 transmit information to central computer 64 in data packets or modules each include a first string of binary bits 86 representing the transmitting station 60a, 60b, a second bit string 88 identifying the patient, a bit group 90 designating the parameter which is being transmitted, another bit group 92 coding the particular measured value of the parameter, a set of bits 94 identifying the point on the patient at which the measurement was taken, and another bit set 96 carrying the time and date of the measurement. Other bit codes may be added as needed.

As shown in FIG. 6, a computerized slide scanning system comprises a slide carrier 100 mountable to a microscope stage and a slide positioning device 102 mechanically linked to the slide carrier 100 for shifting the carrier along a path determined by a computer 104. Computer 104 may be connected to an optional transport or feed assembly 106 which delivers a series of slides (not shown) successively to slide carrier 100 and removes the slides after scanning.

Computer 104 is also connected to an optical system 108 for modifying the magnification power thereof between successive slide scanning phases. Light emerging from optical system 108 is focused thereby onto a charge coupled device ("CCD") 110 connected to computer 104 for feeding digitized video images thereto.

Computer 104 performs a line and texture analysis on the digitized image information from CCD 110 to determine the presence of different organic structures and microorganisms. The different textured regions are parameterized as to size, shape and location and the derived parameters are compared to values in a memory to identify microscopic structures. The texture and line scanning is repeated at different magnification levels.

Computer 104 may be connected to a keyboard 112, a printer 114, and a modem 116. Modem 116 forms part of a telecommunications link for connecting computer 104 to a remote data processing unit such as computer 64 in FIG. 4.

Image generating apparatus 42 in FIG. 1 may take the form of the computerized slide scanning system of FIG. 6.

As shown in FIG. 7, a device for measuring a diagnostic parameter and transmitting the measurement over the telephone lines comprises a monitoring and measuring device 118 which may take the form, for example, of an electronic thermometer, an electronic blood pressure gauge, a pulmonary function apparatus, a doppler study apparatus, an EEG machine, an EKG machine, an EMG machine, or a pressure measurement device, etc., or include a plurality of such components. Monitoring and measuring device 118 is connected at an output to a digitizer 120 which in turn is coupled to a modulator 122. Modulator 122 modulates a carrier frequency from a frequency generator 124 with the data arriving from monitoring and measuring device 118 via digitizer 120 and transmits the modulated signal to an electro-acoustic transducer 126 via an amplifier 128. Transducer 126 is removably attachable via a mounting element 130 to the mouthpiece of a telephone handset (not shown) and generates a pressure wave signal which is converted by a microphone in the handset mouthpiece back to an electrical signal for transmission over the telephone lines. Of course, transducer 126 may be omitted and modulator 122 connected directly to a telephone line.

The system of FIG. 7 enables the transmission of specialized medical data directly over the telephone lines to a central computer (e.g. computer 64 in FIG. 4) which utilizes the incoming data to perform a diagnostic evaluation on the patient.

Monitoring and measuring device 118 may include traditional medical instrumentation such as a stethoscope or modern devices such as a CCD.

Figure 8:
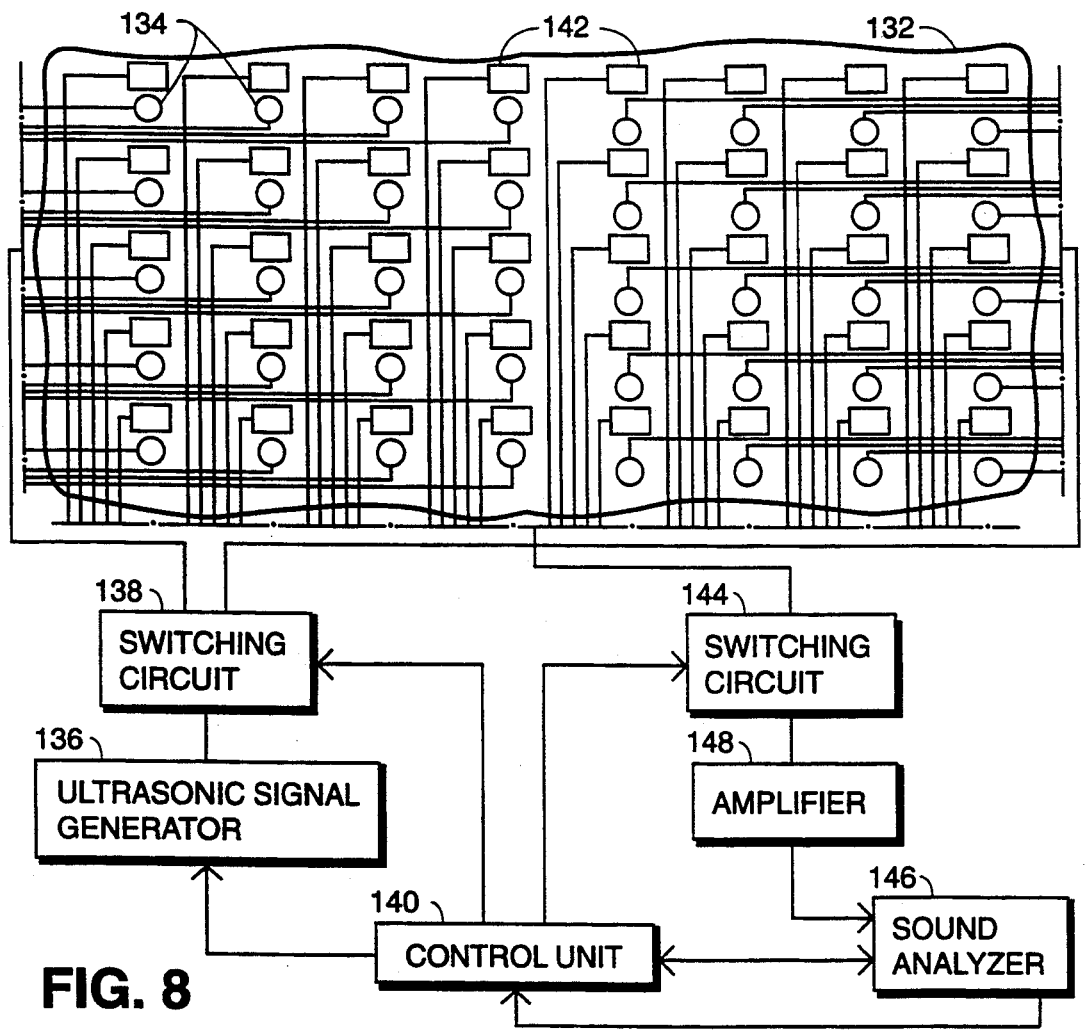
FIG. 8 is a diagram of an ultrasonography device.

FIG. 8 shows an ultrasonographic image generating apparatus which may be used in the medical diagnostic system of FIG. 1 (see reference designation 42) or in the medical diagnostic system of FIG. 4 (see reference designations 78a, 78b, ... 78i). A flexible web 132 carries a plurality of piezoelectric electroacoustic transducers 134 in a substantially rectangular array. Tranducers 134 are each connectable to an ultrasonic signal generator 136 via a switching circuit 138. Switching circuit 138 is operated by a control unit 140 to connect tranducers 134 to signal generator 136 in a predetermined sequence, depending on the area of a patient's body which is being ultrasonically scanned.

Web 132 also carries a multiplicity of acoustoelectric transducers or sensors 142 also arranged in a substantially rectangular array. Sensors 142 are connected to a switching circuit 144 also operated by control unit 140. An output of switching circuit 144 is connected to a sound analyzer 146 via an amplifier 148.

Web 132 is draped over or placed around a portion of a patient's body which is to be monitored ultrasonically. Control unit 140 then energizes signal generator 136 and operates switching circuit 138 to activate transducers 134 in a predetermined sequence. Depending on the transducer or combination of transducers 134 which are activated, control unit 140 operates switching circuit 144 to connect a predetermined sequence of sensors 142 to sound analyzer 146. Sound analyzer 146 and control unit 140 cofunction to determine three dimensional structural shapes from the echoes detected by sensors 142.

Control unit 140 is connected to ultrasonic signal generator 136 for varying the frequency of the generated signal.

Figure 9:
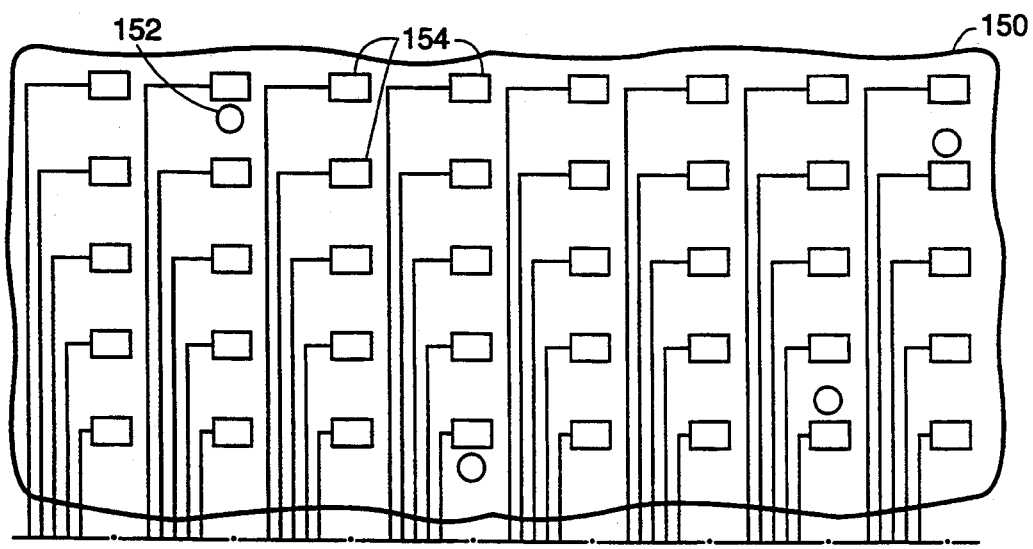
FIG. 9 is a diagram showing a modification of the device of FIG. 8.

FIG. 9 shows a modified ultrasonography web 150 having a limited number of electroacoustic transducers 152 and generally the same number and disposition of sensors 154 as in web 132.

Web 132 or 150 may be substantially smaller than illustrated and may correspondingly carry reduced numbers of transducers 134 and 152 and sensors 142 and 154. Specifically, web 132 or 150, instead of being a sheet large enough to wrap around a torso or arm of a patient, may take a strip-like form which is periodically moved during use to different, predetermined locations on the patient. Control unit 140 and sound analyzer 146 are programmed to detect internal organic structures from the data obtained at the different locations that the web 132 or 150 is juxtaposed to the patient.

As illustrated in FIGS. 10 and 11, a medical diagnostic and treatment system comprises a scanner pad 160 provided on one side with a two-sided (replaceable) adhesive layer 162 which is attachable to the skin of a patient in the region of the spleen or an aortic aneurysm for collecting individualized dimensional data about a splenic hematoma or the aneurysm. Pad 160 carries one or more ultrasonic electroacoustic transducers 164 and a plurality of ultrasonic acoustoelectric transducers 166.

Transducer 164 is connected via a lead 168 to an ultrasonic signal generator 170 disposed in a housing 172 and energized periodically under the control of a microprocessor or computer 174, whereby transducer 164 produces ultrasonic pressure waves of a predetermined frequency and intensity for transmission through the organic tissues of the patient to the subject organ. The ultrasonic pressure waves are reflected by the organ, and particularly by the structural defect thereof, to transducers or sensors 166.

Transducers or sensors 166 are connected via respective leads 176 to a switching circuit 178 operated under the control of microprocessor 174. Ultrasonic-frequency electrical signals generated by transducers 166 are switched by circuit 178 to an amplifer 180 and a digitizer 182. Digitizer 182 is connected at an output to microprocessor 174.

The ultrasonic signals from transducers 166 are analyzed by microprocessor 174 to determined the shape, contours, dimensions, size, etc., of the subject organ or part of the organ. The results of this analysis are stored by microprocessor 174 in a memory 184.

Microprocessor 174 accesses memory 184 to compare previously stored dimensional data with incoming dimensional data to determine whether there has been any significant change in the size of the organ or organ part being monitored. In the event that microprocessor 174 detects such a change, an activating signal is fed by microprocessor 174 to an alarm generator 186. Alarm generator 186 may take the form of an electroacoustic transducer or loudspeaker or some other device which produces a cognizable signal recognized by hospital personnel. Alternatively or additionally, microprocessor 174 sends an electromagnetic activating signal via an optionally wireless transmitter 188 to a remote monitoring facility or station (not shown) in a hospital. An alarm may be generated at the remote station identifying the patient and the dangerous condition. Of course, the signal from microprocessor 174 is coded to identify the patient and the patient's location.

Switching circuit 178, amplifier 180, digitizer 182, microprocessor 174, memory 184, alarm generator 186 are all disposed in housing 172.

The system of FIGS. 10 and 11 further comprises a treatment device 190 operatively connected to microprocessor 174 and adapted for implantation into the patient for therapeutically affecting function of the subject organ to alleviate the possibly dangerous condition. Treatment device 190 specifically includes a balloon 194 inflatable with pressurized fluid from a source 196 upon opening of a valve 198 by microprocessor 174. Pressure source 196 and valve 198 are located in housing 172 and connected to balloon 194 via a catheter 200.

In the event that the organ being monitored is the spleen, balloon 194 and the distal end of catheter 200 are inserted into the femoral artery through the aorta and into the splenic artery. Balloon 194 is thereby positioned upstream of the spleen in the splenic artery. Upon detecting an increase in size of a splenic hematoma in response to the electrically encoded dimensional siganls from transducers 166, microprocessor 174 opens valve 198 and thereby inflates balloon 194 to block the splenic artery and prevent blood flow to the spleen. Hemorrhaging of the spleen from an imminent rupture of the hematoma is thus reduced or avoided.

Housing 172 is provided with a fastener such as a pair of straps 202 and 204 for attaching the housing to the waist of the patient. Alternatively, housing 172 may be provided with a clip (not shown) for securing the housing to a belt worn by the patient.

In an alternative method for monitoring a patient, housing 172 carries a receiver 206 which may be a wireless receiver or may be connectable to a remote facility via a modem (not illustrated). Receiver 206 and transmitter 188 are periodically connected to the remote facility. Upon such a connection, the remote facility instructs microprocessor 174 to provide on a display 208 a message as to where pad 160 is to be placed on the user. Upon a placement of the pad, microprocessor 174 forwards dimension-encoding signals to the remote facility via transmitter 188. Further instructions are subsequently received by receiver 206 and displayed on display 208 under the control of microprocessor 174. Upon the collection of sufficient information, the remote facility may provide a final instruction to the user via display 208. Such a final instruction might be, for example, "Lie down and await ambulance," or "You are fine Call again in an hour."

A keyboard 210 is provided on housing 172 for enabling the user to interact with microprocessor 174 to enable such a procedure. In addition, microprocessor 174 may be reprogrammed via keyboard 210 to periodically monitor the subject organ at intervals of different durations. Keyboard 210 is used to initialize and calibrate microprocessor 174.

Figure 12:
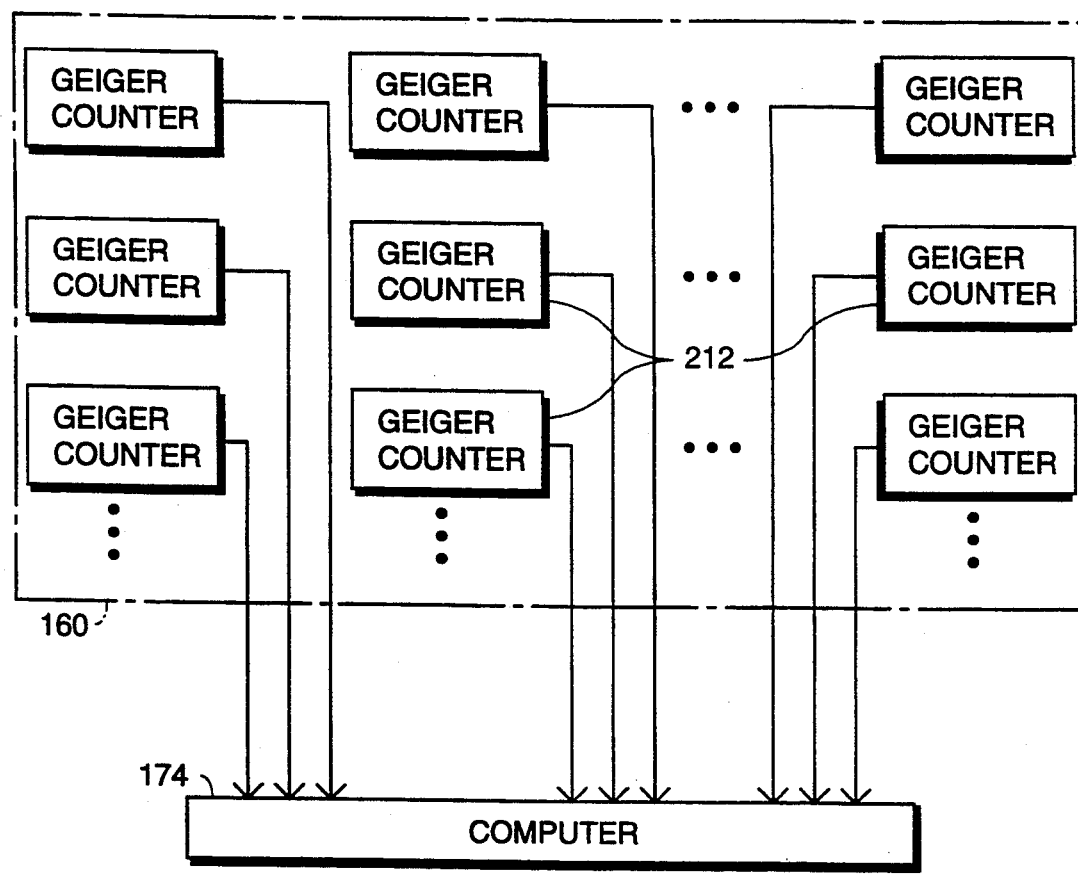
FIG. 12 is a block diagram of parts of a modification of the system of FIGS. 10 and 11.

FIG. 12 illustrates that the ultrasonic transducers 166 of the embodiment of FIGS. 10 and 11 may be replaced by a plurality of Geiger type counters 212 for monitoring the products of radiactive decay. In this case, a radioactive substance is injected or otherwise dispensed within the body so as to be absorbed, for example, into the spleen. As the substance decays, the radioactive byproducts reveal the dimensions (shape, configuration, size) of the organ and its parts.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical method comprising the steps of:
scanning a predetermined internal organ of a patient;
storing dimensional data obtained during said step of scanning and relating to dimensions of said organ;
automatically comparing the dimensional data obtained during said step of scanning with stored previously determined data relating to dimensions said organ; and
upon determining in said step of comparing that said organ has undergone a change in its dimensions indicating a possibly dangerous condition of the patient, automatically treating the patient therapeutically to alleviate the possibly dangerous condition.

2. The method defined in claim 1 wherein said step of therapeutically affecting includes the step of at least reducing blood flow to the organ.

3. The method defined in claim 2 wherein said step of reducing includes the step of inflating a balloon in an artery feeding the organ to thereby block blood flow in said artery.

4. The method defined in claim 1 wherein said step of generating includes the steps of connecting a transmitter device to a modem and transmitting an electromagnetic signal over telephone lines to a remote monitoring facility.

5. The method defined in claim 4 wherein said electromagnetic signal is a wireless signal, said step of transmitting includes the step of wirelessly transmitting said wireless signal.

6. The method defined in claim 1, further comprising the step of attaching a scanning device to the patient.

7. The method defined in claim 1, further comprising the steps of (a) transmitting the dimensional data to a remote monitoring facility, (b) receiving instructions from said facility, and (c) manually moving a scanning device from one location to another in response to said instructions, each such location being juxtaposed to the patient.

8. The method defined in claim 1 wherein said step of scanning includes the steps of generating an ultrasonic pressure wave, monitoring said pressure wave upon reflection thereof by internal organs, and generating an electrical signal encoding the reflected ultrasonic pressure wave.

9. The method defined in claim 1 wherein said step of scanning includes the step of detecting byproducts of radioactive decay.

10. The method defined in claim 1 wherein the organ is a spleen.

11. The method defined in claim 1 wherein the organ is a blood vessel.

12. The method defined in claim 1, further comprising the step of automatically generating a cognizable signal upon determining in said step of comparing that said organ has undergone said change in its dimensions.

13. The method defined in claim 1 wherein said step of affecting includes the step of operating a device at least partially inserted into the patient.

14. A medical method comprising the steps of:
attaching a scanning device to a patient;
operating said scanning device to scan a predetermined internal organ of the patient;
storing dimensional data obtained during said step of scanning and relating to dimensions of said organ;
automatically comparing the dimensional data obtained during said step of scanning with stored previously determined data relating to dimensions of said organ so as to determine whether said organ has undergone a change in its dimensions indicating a possibly dangerous condition of the patient; and
upon determining in said step of comparing that said organ has undergone said change in its dimensions, automatically generating a cognizable signal.

15. The method defined in claim 14 wherein said step of generating includes the step of transmitting an electromagnetic signal to a remote monitoring facility.

16. The method defined in claim 14, further comprising the steps of (a) transmitting the dimensional data to a remote monitoring facility, (b) receiving instructions from said facility, and (c) manually moving said scanning device from one location to another in response to said instructions, each such location being juxtaposed to the patient.

17. The method defined in claim 14 wherein said step of scanning includes the step of detecting byproducts of radioactive decay.

18. The method defined in claim 14 wherein the dimensional data relates to external dimensions of said organ.

19. A medical system comprising:
scanning means juxtaposable to a patient for collecting individualized dimensional data about a predetermined internal organ of the patient;
memory means operatively connected to said scanning means for storing the dimensional data obtained by said scanning means at different times;
computing means operatively connected to said memory means for comparing the dimensional data obtained at one time with the dimensional data obtained at a subsequent time so as to determine whether said organ has undergone a change in its dimensions indicating a possibly dangerous condition of the patient; and
treatment means operatively connected to said computing means and adapted for at least partial implantation into the patient for therapeutically affecting the patient to alleviate the possibly dangerous condition upon the determination by said computing means that said organ has undergone a change in its dimensions indicating said possibly dangerous condition.

20. The system defined in claim 19 wherein said treatment means includes means for at least reducing blood flow to the organ upon the determination by said computing means that the organ has undergone a change in its dimensions indicating said possibly dangerous condition.

21. The system defined in claim 20 wherein said means for reducing includes a balloon disposable in an artery feeding the organ and inflation means operatively connected to said balloon for inflating said balloon for blocking blood flow in said artery upon the determination by said computing means that dimensions of the organ have changed so as to indicate a possibly dangerous condition.

22. The system defined in claim 19 wherein said scanning means is portable, further comprising fastener means for attaching said scanning means to the patient.

23. The system defined in claim 19 wherein said scanning means includes electroacoustic transducer means for generating an ultrasonic pressure wave and acoustoelectric transducer means for generating an electrical signal encoding reflected ultrasonic pressure waves received by said scanning means.

24. The system defined in claim 19 wherein said scanning means includes detector means for detecting by-products of radioactive decay.

25. The system defined in claim 19, further comprising alarm means operatively connected to said computing means for generating a cognizable signal upon a determination by said computing means that dimensions of the organ have changed so as to indicate a possibly dangerous condition of the patient.

26. The system defined in claim 25 wherein said alarm means includes transmitter means for transmitting to a remote monitoring facility an electromagnetic signal encoding the change in dimensions of the organ.

27. The system defined in claim 26 wherein said electromagnetic signal is a wireless signal, said transmitter means including means for generating and transmitting said wireless signal.

28. A medical method comprising the steps of:
scanning a predetermined internal organ of a patient to determine external dimensions of said organ as defined between outwardly facing surfaces of said organ;
storing dimensional data obtained during said step of scanning and relating to external dimensions of said organ as defined between outwardly facing surfaces of said organ;
automatically comparing the dimensional data obtained during said step of scanning with stored previously determined data relating to external dimensions of said organ so as to determine whether said organ has undergone a change in its external dimensions indicating a possibly dangerous condition of the patient; and
upon determining in said step of comparing that said organ has undergone said change in its external dimensions, automatically generating a cognizable alarm signal.

* * * * *